STRAWBERRY PLANT

Filed July 25, 1969 2 Sheets-Sheet 1

By Townsend and Townsend

INVENTORS
ROYCE S. BRINGHURST
VICTOR VOTH

STRAWBERRY PLANT

Filed July 25, 1969 2 Sheets-Sheet 2

By Townsend and Townsend

INVENTORS
ROYCE S. BRINGHURST
VICTOR VOTH

United States Patent Office

Plant Pat. 3,178
Patented May 16, 1972

3,178
STRAWBERRY PLANT

Royce S. Bringhurst, Davis, and Victor Voth, Santa Ana, Calif., assignors to The Regents of the University of California, Berkeley, Calif.

Filed July 25, 1969, Ser. No. 845,103
Int. Cl. A01h 5/03
U.S. Cl. Plt.—48 1 Claim This invention relates to a new and distinct variety of strawberry plant designated Sequoia which is the result of a cross between two University of California seedling selections, Cal 51s1–1 and Cal 52.16–15 (both unpatented).

The original seedling was fruited and selected at the South Coast Field Station of the University of California, Santa Ana, Calif. in 1958 and through asexual reproduction subsequently underwent testing in experimental plantings throughout California as Cal 56.124–12.

Typical plant, flower and fruit characteristics are presented in the accompanying color photographic reproductions:

Figure 1:
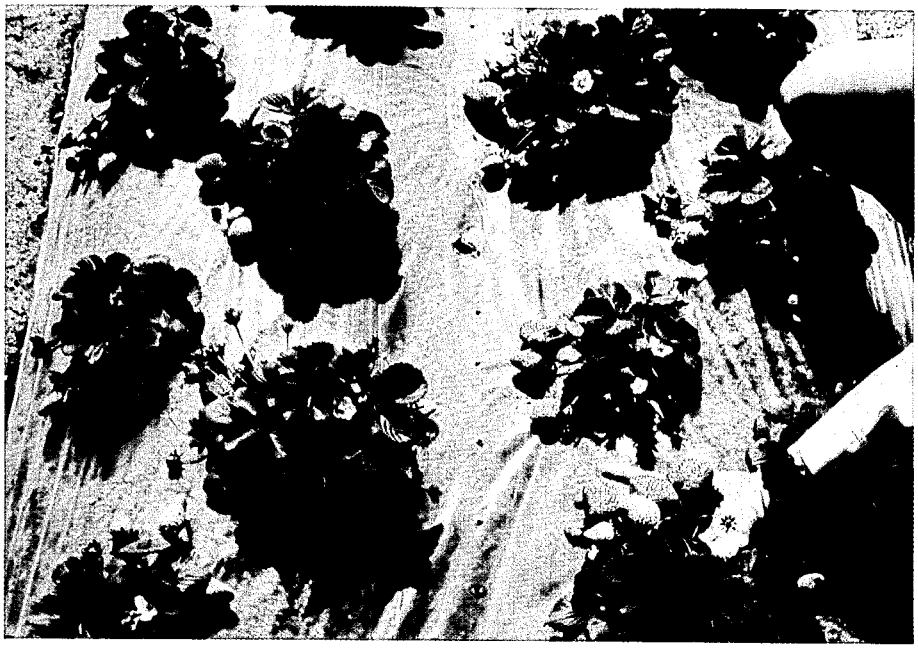
FIG. 1 shows the entire plant as it appears in full production following winter planting from high elevation plants in an experimental planting in southern California.
Figure 2:
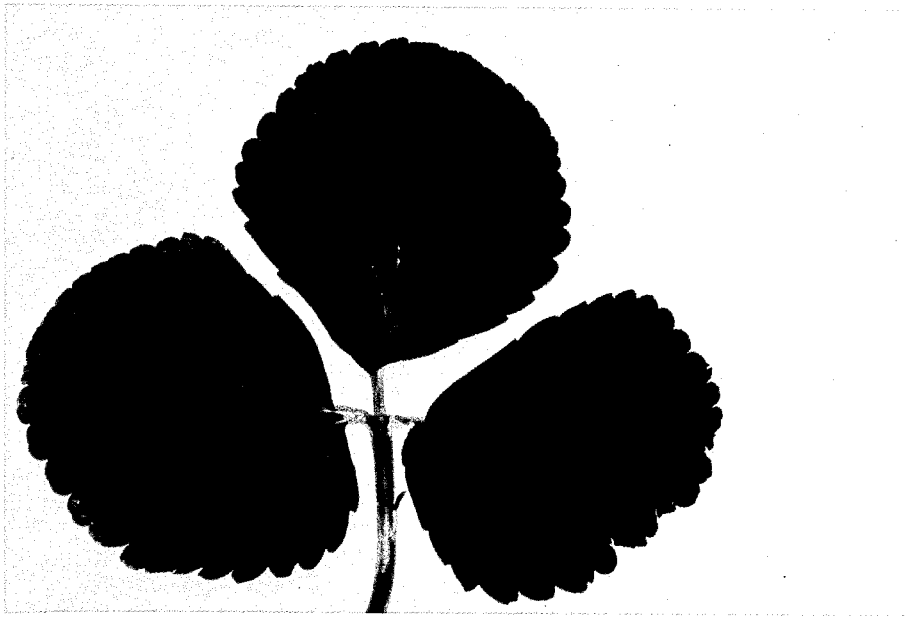
FIG. 2 shows a typical leaf, dark green color, almost round terminal leaflet and relatively long petiolules.
Figure 3:
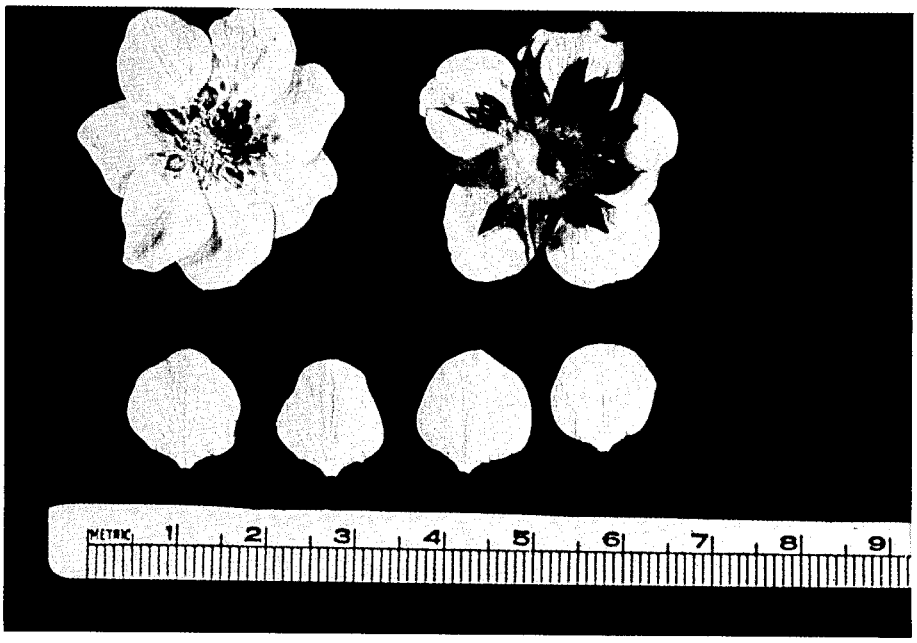
FIG. 3 shows the typical flower (a) top view with relatively short stamens, abundant pollen and 6 to 7 petals, (b) underview with primary and secondary sepals almost equal to size, and (c) petals, large and rounded.
Figure 4:
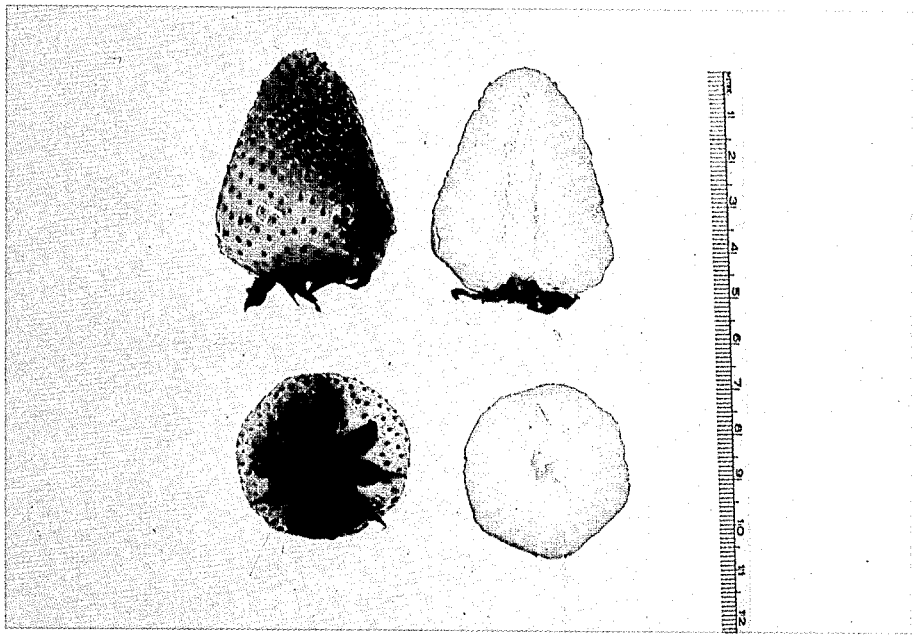
FIG. 4 shows typical early season fruit, long-conic in shape, and round in cross section.

The new variety is a non-everbearing, erect growing canopy type, medium to large in size and of great vigor. The color is slightly darker than that of the Tioga variety or that of the Goldsmith variety described in Plant Patent No. 1,735. The leaves cup upward and are semi-rugose. It is characterized by high runner production and early plant maturity in California high elevation nurseries. This contributes to its adaptation to early winter planting in southern California.

The most important distinguishing characteristic of this new variety is the unique combination of a very low chilling requirement and very low threshold temperature for vigorous growth in comparison with other California varieties. Thus, it may be planted earlier than other winter planting varieties and will reach full production earlier. Sequoia is further characterized by maximum flexibility under the winter planting system in that it has performed uniformly well on plantings made at the earliest practicable planting dates for high elevation plants (about October 1) through the latest (about November 20), with and without cold storage.

The fruit is large, attractive and generally free of defects that detract from its appearance. The skin of the fruit is relatively tender when the fruit is fully ripe compared with that of Tioga although the flesh is firm. It must be picked at frequent intervals in order to maintain quality. It is easy to harvest since it is borne on relatively long inflorescences and detaches easily at the base of the calyx.

The dessert quality of the fruit is excellent. This is a subjective trait but the combination of high sugar, subacidity and aromatic components that characterizes the flavor of Sequoia is highly pleasing.

The plants of Sequoia are markedly superior to varieties like Tioga in tolerance to common leaf spot (Mycosphaerella), the most serious disease problem in winter planted California strawberries. It also appears to be quite tolerant to angular leaf spot (Xanthomonas), a problem with winter planted Fresno, Shasta and Salinas. Sequoia plants are susceptible to Verticillium wilt. They are affected by two-spotted mite about as much as Tioga which is much less than Shasta, a highly susceptible variety.

*Vegetative and floral characteristics (winter planted plants in coastal California)*

Foliage: Medium high canopy; very vigorous and about as tolerant of salinity as Lassen.

Root system: Extensive, much branched and vigorous.

Leaves: Large, cupped upward; terminal leaflet almost round; terminal petiolule length about 9% of that of terminal leaflet; pubescence medium; color, moderate Olive Green 5GY 4/3 (Nickerson Color Fan).

Runners: Numerous and new plants set readily; 50:1 common in the nursery.

Inflorescence: Medium long, much branched, flowers large with 6 to 7 petals; stamens short; pollen abundant; normally sets well.

*Fruit characteristics*

Shape: Long conic, round in cross section.

Size: Large, averaging about 18 grams. Fruit; largest over 30 grams.

Surface: Smooth and regular, glossy; skin somewhat tender.

Color: Strong Red 5R 4/12; darkens when over-ripe; ripens unevenly at times.

Flesh: Firm but juicy; color similar to surface but lighter toward core.

Core: Fruit mostly solid but larger fruits have medium sized cavity; the core is small and may or may not remain with the fruit when the calyx is removed.

Seeds: Medium sized yellow to reddish yellow: set even with surface.

Calyx: Medium large, 30 to 35 mm. in diameter; secondaries only slightly smaller than primaries.

Production: Exceptionally heavy under the California Winter Planting System.

We claim:

1. A new and distinct strawberry variety described and illustrated, and characterized particularly by its low chilling requirement, ability to grow at relatively low temperature and great flexibility under the winter planting system; its exceptionally large fruit size of long conic shape, excellent dessert quality and high productivity under the winter planting system in coastal California.

References Cited

American Fruit Grower, Western Edition, May 1969, p. 40A relied on.

ROBERT E. BAGWILL, Primary Examiner